United States Patent [19]

Ward et al.

[11] Patent Number: 5,225,419
[45] Date of Patent: Jul. 6, 1993

[54] CERTAIN 1,8-ETHANO OR PROPANO-1,4-DIHYDRO-4-OXO-QUINOLINE-3-CARBOXAMIDES AND DERIVATIVES THEREOF

[75] Inventors: Terence J. Ward, Maidenhead; Janet C. White, Wokingham, both of England

[73] Assignee: John Wyeth & Brother, Limited, Maidenhead, England

[21] Appl. No.: 760,299

[22] Filed: Sep. 16, 1991

Related U.S. Application Data

[62] Division of Ser. No. 595,333, Oct. 10, 1990, Pat. No. 5,096,901.

[30] Foreign Application Priority Data

Oct. 14, 1989 [GB] United Kingdom ............... 8923209
May 4, 1990 [GB] United Kingdom ............... 9010085

[51] Int. Cl.$^5$ ............... C07D 455/04; C07D 471/04; A61K 31/44
[52] U.S. Cl. ............... 514/287; 514/294; 546/65; 546/94; 546/90; 546/112; 546/133; 546/134; 546/136; 546/137; 548/454
[58] Field of Search ............... 546/94, 65; 514/294, 514/287

[56] References Cited

FOREIGN PATENT DOCUMENTS

| | | | |
|---|---|---|---|
| 0382687 | 8/1980 | European Pat. Off. ............ | 544/284 |
| 0200444 | 11/1986 | European Pat. Off. ............ | 546/126 |
| 3827253 | 3/1989 | Fed. Rep. of Germany ...... | 546/126 |
| WO8403281 | 8/1984 | PCT Int'l Appl. ............ | 546/126 |
| 2145416 | 3/1985 | United Kingdom ............ | 546/126 |
| 2125398 | 11/1986 | United Kingdom ............ | 546/133 |

OTHER PUBLICATIONS

Pat. Abst. of Japan 13:326, C620; abstract of JP 01-104072.
Chem. Absts. 111:194610c (1989).

*Primary Examiner*—Alan L. Rotman
*Attorney, Agent, or Firm*—Arnold S. Milowsky

[57] ABSTRACT

Compounds of formula

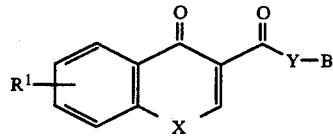

wherein
$R^1$ is hydrogen or one or more specified substituents,
X is —O— or —NR$^2$— where $R^2$ is lower alkyl, lower alkenyl, lower alkynyl, aryl or specified substituted lower alkyl or $R^2$ represents a group —Z— which is connected to the 8-position of the aromatic ring so as to form a heterocyclic ring of 5 to 7 ring members,
Y is O or NR$^3$ where $R^3$ is hydrogen or lower alkyl, and
B is a saturated azabicyclic ring (eg tropanyl or quinuclidinyl) or a N-oxide thereof
and their acid addition salts are 5-HT$_3$ antagonists which may be used in, for example, the treatment of neuro-psychiatric disorders.

5 Claims, No Drawings

CERTAIN 1,8-ETHANO OR PROPANO-1,4-DIHYDRO-4-OXO-QUINOLINE-3-CARBOXAMIDES AND DERIVATIVES THEREOF

This is a division of application Ser. No. 07/595,333, filed Oct. 10, 1990, now U.S. Pat. No. 5,096,901.

This invention relates to heterocyclic compounds. In particular the invention relates to novel amides and esters, to processes for their preparation, to their use and to pharmaceutical compositions containing them. The novel compounds of the invention are useful as antagonists of specific 5-hydroxytryptamine (5-HT) receptors as explained hereinbelow. A number of prior patent specifications disclose 5-HT$_3$ antagonists of various structures e.g. EP-A-0200444, GB-A-2153821, GB-A-2125398 and EP-A-323077. The novel compounds of the present invention are those of the general formula

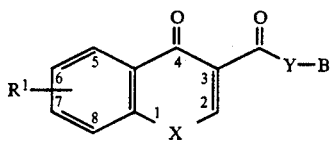

(I)

and the pharmaceutically acceptable acid addition salts thereof. In this formula $R^1$ represents hydrogen or one or more substituents selected from lower alkyl, hydroxy, lower alkoxy, halogen, methylenedioxy, halo(lower)alkyl, nitro, amino, (lower)alkylamino and di(lower)alkylamino X represents —O— or —NR$^2$— where R$^2$ represents lower alkyl, lower alkenyl, lower alkynyl, cyclo(lower)alkyl, cyclo(lower)alkyl-loweralkyl, aryl, aryl(lower)alkyl, a group of formula —(CH$_2$)$_r$—Y'—R$^8$ (where r is an integer of 1 to 4, Y is O, S or NR$^5$, where R$^5$ is hydrogen or lower alkyl and R$^8$ is hydrogen, lower alkyl or cycloloweralkyl) or a group of formula —Z— which is connected to the 8-position of the aromatic ring so as to form a heterocyclic ring of 5 to 7 ring members wherein the ring members represented by Z are one or more methylene groups (optionally substituted by one or more lower alkyl groups) and optionally a hetero group selected from O, S, SO$_2$ or NR$^5$ where R$^5$ is hydrogen or lower alkyl Y represents O or NR$^3$ where R$^3$ is hydrogen or lower alkyl and B represents a saturated azabicyclic ring or an N-oxide thereof wherein the saturated azabicyclic ring has the formula

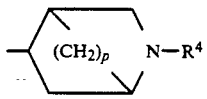

(II)

where m is 2,3 or 4 and R$^4$ is hydrogen, or (lower)alkyl, or

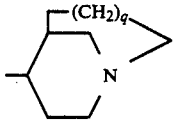

(III)

or

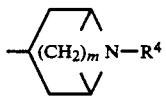

(IV)

where p is 1, 2 or 3 and R$^4$ has the meaning given above or

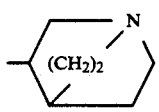

(V)

where q is 0, 1 or 2.

The term "lower" as used herein means that the radical referred to contains up to 6 carbon atoms. The radical preferably contains up to 4 carbon atoms. For example, a lower alkyl group may be straight chain or branched and may be methyl, ethyl, propyl or butyl. A preferred example of lower alkenyl is allyl. A lower alkoxy group may be, for example, methoxy, ethoxy, propoxy or butoxy. A cyclo(lower)alkyl group may be, for example, cyclopropyl, cyclobutyl, cyclopentyl or cyclohexyl. An aryl group is preferably a phenyl group which may be optionally substituted by one or more substituents such as those mentioned above for R$^1$. When R$^1$ represents one or more halogen substituents such substituents are preferably chlorine or fluorine. A halo(lower)alkyl substituent is preferably trifluoromethyl. A preferred example of cyclo(lower)alkyl-lower alkyl is cyclopropylmethyl. An aryl(lower)alkyl group is preferably benzyl or substituted benzyl in which the substituents may be, for example, those mentioned above in connection with R$^1$ When X represents —NR$^2$— where R$^2$ represents —Z— the compounds have the formula

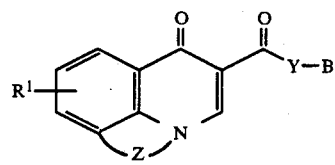

In the formula prefered examples of Z include —(CH$_2$)$_n$— where n is 2 or 3, an alkyl substituted di- or tri-methylene chain, eg. —CH$_2$ CH(lower alkyl)—, —CH$_2$ C(lower alkyl)$_2$— or a chain comprising an alkylene group (optionally substituted by lower alkyl) and a hetero group e.g. —OCH$_2$—, —OC(lower alkyl)$_2$—, —S.CH$_2$CH$_2$— and —CH$_2$OCH$_2$—

In the radical of formula (II), preferably m is 2 and R$^4$ is lower alkyl, preferably methyl. The radical in which m is 2 and R$^4$ is methyl is known as tropan-3-yl, otherwise 8-methyl-8-azabicyclo[3.2.1]octan-3-yl.

The radical of formula (III) is known as quinuclidinyl, otherwise 1-azabicyclo[2.2.2]octan-3-yl.

In the radical of formula (IV) preferably p is 2, and R$^4$ is preferably C$_{1-4}$ alkyl, particularly methyl.

In the radical of formula (V), q is preferably 1.

The compounds of the invention may contain one or more asymmetric carbon atoms so that the compounds can exist in different stereoisomeric forms. The compounds can, for example, exist as racemates or optically active forms. The optically active forms can be obtained by resolution of the racemates or by using an optically active form of the starting material in the processes described hereinafter. Furthermore, radicals such as those of formulae (II) and (IV) can exist in different configurations corresponding to the endo configuration as in tropine and the exo configuration as in pseudotropine. The endo configuration is preferred. The compounds of the invention may be prepared by methods known in the art from known starting materials or starting materials that may be prepared by conventional methods. In one method of preparing an amide of formula (I) where Y is —NR$^3$, an amine of formula

NHR$^3$B           (VI)

where R$^3$ and B as defined above is acylated with an acid of formula

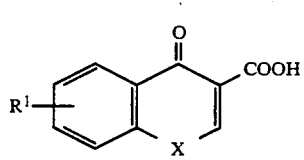
(VII)

(where R$^1$ and X are as defined above) or with an acylating derivative thereof. Examples of acylating derivatives include the acid halides (e.g. acid chlorides), azides, anhydrides, imidazolides (e.g. obtained from carbonyldiimidazole), activated esters or O-acyl ureas obtained from a carbodiimide such as a dialkylcarbodiimide, particularly dicyclohexylcarbodiimide. Preferably the amine is acylated with the acid in presence of a coupling agent such as dicyclohexylcarbodiimide, 1,1'-carbonyldiimidazole, iso-butylchloroformate or diphenylphosphinyl chloride.

An ester of the invention in which Y is —O— may be prepared by esterification of the acid of formula (VII) with an alcohol of formula

B—OH           (VIII)

(where B has the meaning given above). Esterification may be carried out by the general methods known in the art. For example, the alcohol may be reacted with an acid halide, eg in the presence of an acid acceptor.

The acids of formula (VII) are known or may be prepared by known methods. For example, the acid in which X is —NR$^2$— may be prepared by the following reaction scheme:

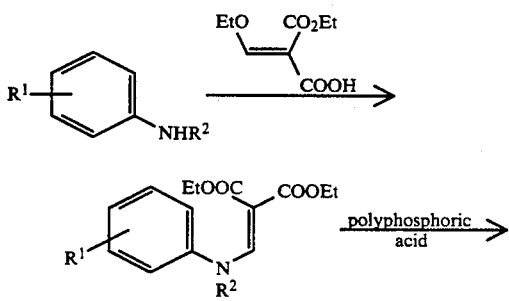

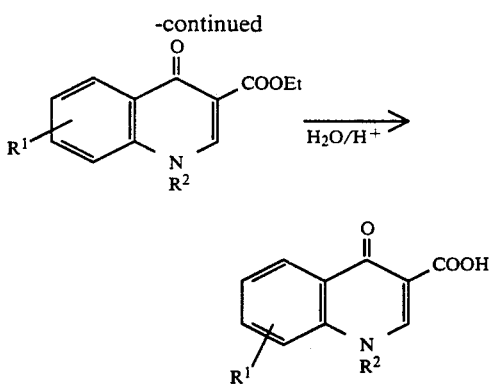

An alternative method of preparing the amides of the invention (Y=—NR$^3$—) comprises cyclising a compound of formula

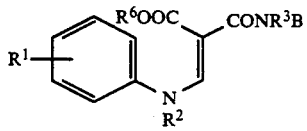
(IX)

where R$^1$, R$^2$, R$^3$ and B are as defined above and R$^6$ is (lower)alkyl, e.g. ethyl. The cyclisation can be carried out in presence of a cyclodehydrating agent such as polyphosphoric acid. The starting material of formula (IX) may be prepared by reacting an amine of formula

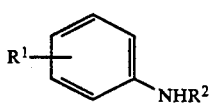
(X)

(where R$^1$ and R$^2$ are as defined above) with an unsaturated compound of formula

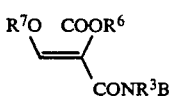
(XI)

where R$^3$, R$^6$ and B are as defined above and R$^7$ is (lower)alkyl, preferably ethyl. The reaction can be carried out by heating the reactants alone or in presence of a suitable solvent.

An alternative method of preparing the compounds of the invention in which X is —NR$^2$— where R$^2$ is lower alkyl, cyclo(lower)alkyl, cyclo(lower)alkyl-lower alkyl, aryl, aryl(lower)alkyl or —(CH$_2$)$_r$—Y'—R$^8$ comprises cyclisation of a compound of formula

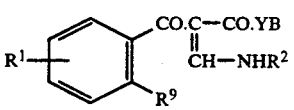
(XII)

where R$^1$, R$^2$, Y and B are as defined above and R$^9$ is a leaving group such as halogen (e.g. fluorine or chlorine) or an alkyl- or aryl-sulphonyloxy group. The cyclisation may be effected by treatment with a strong base, e.g. sodium hydride. The starting material of formula (XII) may be prepared by methods known for analogous compounds.

Compounds of the invention in which X is —NR$^2$— where R$^2$ is lower alkyl, lower alkenyl, lower alkynyl, cyclo(lower)alkyl, cyclo(lower)alkyl-lower alkyl, aryl, aryl(lower)alkyl or —(CH$_2$)$_r$—Y'—R$^8$ can be prepared alkylation of the corresponding compound in which X is —NH—. The alkylation may be carried out, for example, by reaction with a (lower)alkyl, lower alkenyl, lower alkynyl, cyclo(lower)alkyl, cyclo(lower)alkyl-lower alkyl, aryl, aryl(lower)alkyl or —(CH$_2$)$_r$—Y'—R$^8$ halide in presence of a base. The starting compound in which X is —NH— may be prepared in an analogous manner to that described above from an appropriately substituted compound (VII).

The compounds of the invention in which B represents the N-oxide of the radicals (II) to (V) may be prepared by oxidising a compound in which B represents the radicals (II) to (V) with, for example, hydrogen peroxide or a peracid. If in any of the above processes a reactant contains groups that would be affected under the reaction conditions employed for the reaction the group may be protected and the protecting group subsequently removed.

If in the processes described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the present invention possess pharmacological activity. In particular they antagonise specific 5-hydroxytryptamine (5-HT) receptors in warm blooded animals. Specifically the compounds possess 5-HT$_3$ antagonistic activity and hence are of value in conditions where antagonism of 5-HT$_3$ receptors is desirable. 5-HT$_3$-antagonists are also termed "antagonists of "neuronal" 5-hydroxytryptamine receptors" and "serotonin (5-hydroxytryptamine) M-receptor antagonists".

The compounds of the invention are tested for 5-HT$_3$ antagonistic activity in the rat vagus by the following procedure:

The method is similar to that described by Ireland and Tyers, Br. J. Pharmac., 1987, 90, 229–238 and is dependent upon the ability of 5-HT to depolarize the vagus nerve in vitro.

Segments of the vagus nerve from Sprague-Dawley rats were placed in a perspex chamber and perfused with Krebs solution. Electrodes, positioned at either end of the nerve segment, were used to record the potential differences which ensued upon the addition of various concentrations of 5-HT to one end of the nerve segment. Concentration-response curves to 5-HT were obtained in this manner prior to and following equilibration of the nerve segment with Krebs solution containing the test-substance. A Schild analysis was performed on these results in order to obtain a measure of antagonist potency, expressed as a pA$_2$ value. When tested by this procedure (endo)-N-[8-aza-8-methylbicyclo[3.2.1]octan-3-yl]-1-methylquinolin-4-one-3-carboxamide, a representative compound of the present invention, had a pA$_2$ of 8.4

The invention further provides a compound of formula (I) or a pharmaceutically acceptable acid addition salt thereof for use in antagonising 5-HT$_3$ receptors in a mammal.

5-HT$_3$ antagonists may be useful in the treatment of neuro-psychiatric disorders such as anxiety, psychotic disorders (e.g. schizophrenia), dependency on drugs or other substances of abuse, cognitive disorders; in the treatment of gastro-intestinal disorders such as emesis and nausea and in the treatment of migraine. Accordingly the invention provides the use of a compound of the invention for use in one or more of the above mentioned treatments. The invention also provides a method for one or more of the above mentioned treatments which comprises administering to a warm blooded animal in need thereof an effective amount of the compound of the invention.

For certain of the above mentioned conditions it is clear that the compounds may be used prophylactically as well as for the alleviation of acute symptoms References herein to "treatment" or the like are to be understood to include such prophylactic treatment, as well as treatment of the acute conditions.

The anti-emetic properties of the compounds are particularly advantageous in the treatment of nausea and vomiting associated with cancer chemotherapeutic agents and radiation therapy. The compounds are therefore of use in the treatment of cancer by chemotherapeutic agents (cytotoxic or cytostatic agents such as cisplatin, doxorubicin and cyclophosphamide) as well as irradiation. Accordingly, the invention also provides a product containing a cancer chemotherapeutic agent and a compound of the invention as a combined preparation for simultaneous, separate or sequential use in cancer therapy.

In a further aspect the invention provides a pharmaceutical composition comprising a compound of the invention in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80%, of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredients, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

The compounds of the invention can also be administered by the nasal route. When formulated for nasal administration the compositions may comprise a compound of the invention in a liquid carrier; such compositions may be administered for example in the form of a spray or as drops. The liquid carrier may be water (which may contain further components to provide the desired isotonicity and viscosity of the composition). The composition may also contain additional excipients such as preservatives, surface active agents and the like. The compositions may be contained in a nasal applicator that enables the composition to be administered as drops or as a spray. For administration from an aerosol container the composition should also include a propellant.

Pharmaceutical compositions for treatment and/or prevention of nausea or vomiting may contain a cyclo-oxygenase inhibitor in addition to a compound of the invention. Examples of cyclo-oxygenase inhibitors include systemic NSAID's e.g. indomethacin, piroxicam.

Preferably the pharmaceutical composition is in unit dosage form, eg as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquids. The unit dosage form can be, for example, a capsule or tablet itself, or it can be the appropriate number of any such compositions in package form.

The quantity of the active ingredient in unit dose of composition may be varied or adjusted from 0.5 mg or less to 750 mg or more, according to the particular need and the activity of the active ingredient.

The invention also includes the compounds in the absence of the carrier where the compounds are in unit dosage form.

The following Examples illustrates the invention.

EXAMPLE 1

(Endo)-N-(8-methyl-8-azabicyclo[3.2.1]octan-3-yl)-1,4-dihydro-1-methyl-4-oxoquinoline-3-carboxamide A suspension of 1,4 dihydro-1-methyl-4-oxoquinoline-3-carboxylic acid (1.02 g, 5 mmol) and carbonyldiimidazole (0.85 g, 5 mmol) in dimethylformamide (15 ml) was stirred and heated at 80° C. for 0.5 hour to give a clear solution. (Endo)-3-aminotropane dihydrochloride (1.06 g, 5 mmol) was then added, followed by addition of triethylamine (1.3 g) and the reaction stirred at 80° C. for a further 2 hours. The mixture was then cooled, diluted with water (25 ml) and the precipitated product (1.2 g) collected, and recrystallised from water (150 ml) to give 0.7 g of the title base. The base was dissolved in ethanol (7 ml) and acidified with ethereal hydrogen chloride to precipitate the title compound as the hydrochloride (0.55 g), mp.>300° C.

EXAMPLE 2

(Endo)-N-(8-methyl-8-azabicyclo[3.2.1.]octon-3-yl)-1,4-dihydro-1-butyl-4-oxoquinoline-3-carboxamide A mixture of 1-butyl-1,4-dihydro-4-oxoquinoline-3-carboxylic acid (0.98 g, 4 mmol), carbonyldimidazole (0.7 g, 4.4 mmol) and dimethylformamide (12 ml) was stirred at 80° C. for 1.5 hours. (Endo)-3-aminotropane (0.56 g, 4 mmol) was then added and stirring continued for a further 1.5 hours at the same temperature. The solvent was removed and the residue diluted with ice-water (15 g).

The precipitated solid was collected, washed with ice-cold water and air dried. The base was dissolved in a hot mixture of water (5 ml) and ethanol (3 ml), then ice-cooled and basified to pH 11 by addition of concentrated aqueous ammonia to precipitate the crystalline product which was collected and washed with cold dilute ammonia solution. The purified base (0.82 g) was then dissolved in ethanol (8 ml), acidified with ethanolic HCl and diluted with ether (3 ml). Ice-cooling gave the product as the hydrochloride (0.49 g) mp. 267-268° C.

EXAMPLE 3

(Endo)-N-(8-methyl-8-azabicyclo[3.2.1]octan-3-yl)-1-benzyl-1,4-dihydro-4-oxoquinoline-3-carboxamide 1-Benzol-1,4-dihydro-4-oxoquinoline-3-carboxylic acid (1.96 g, 7.03 mmol) in dry DMF (20 ml) was treated with carbonyl diimidazole (1.14 g, 7.04 mmol) at room temperature and the mixture heated at 80° C. for 3 hours. (Endo)-3- aminotropane (0.99 g, 7.07 mmol) was added and heating continued overnight (19 hours) to give a suspension. The mixture was diluted with water (40 ml) and the pH adjusted to 9-10 by addition of concentrated aqueous potassium carbonate. The solid was collected, washed well with water, dried and recrystallised from ethanol (20 ml) and water (20 ml) to give the product free base (1.72 g). This was dissolved in boiling ethanol (15 ml) and the solution acidified with ethanolic hydrogen chloride. The resulting precipitate was collected, washed with ethanol and dried at 80° C. in vacuo to give the title compound as the hydrochloride, hydrate, one-third ethanolate (1.91 g), mp 296° to 297° C.

EXAMPLE 4

(Endo)-N-(8-aza-8-methylbicyclo[3.2.1]octan-3-yl)chromone-3-carboxamide (a) A mixture of chromone-3-carboxylic acid (1.25 g) and thionyl chloride (6 ml) was heated at reflux for 5 minutes. The reaction mixture was then diluted with cyclohexane (15 ml) and ice-cooled. The crystalline precipitate was collected by filtration, washed with cyclohexane and dried under vacuum to give chromone-3-carbonyl chloride (1.2 g).

(b) A solution of chromone-3-carbonyl chloride (1.04 g, 5 mmol) in $CH_2Cl_2$ (20 ml) was added dropwise over about 5 minutes to an ice-cooled stirred mixture of (endo)-3-aminotropane (0.7 g, 5 mmol), anhydrous $K_2CO_3$ (3 g) and $CH_2Cl_2$ (20 ml). After addition was complete, stirring was continued for a further 0.5 hour and the mixture diluted with water (50 ml). The organic phase was separated, dried ($Na_2SO_4$) and evaporated to give a solid (1.7 g). The base was dissolved in ethanol (15 ml) and acidified with ethanolic HCl to precipitate crude hydrochloride (0.9 g). Recrystallization three times from ethanol gave the title compound as pure hydrochloride (0.3 g), mp.>300° C.

EXAMPLE 5

(Endo)-N-(9-methyl-9-azabicyclo[3.3.1]nonan-3-yl)-1,4-dihydro-1-methyl-4-oxoquinoline-3-carboxamide A suspension of 1,4-dihydro-1-methyl-4-oxoquinoline-3-carboxylic acid (1.02 g, 5 mmol) and carbonyldiimidazole (0.85 g, 5 mmol) in DMF (15 ml) was stirred and heated at 85° for 3 hours to give a clear solution. (Endo)-3-aminohomotropane dihydrochloride (1.13 g, 5 mmol) and diisopropylethylamine (1.29 g, 10 mmol) were added and heating continued overnight (19 hours). The solution was cooled to room temperature and diluted with water (25 ml). The pH was adjusted to 10-11 by addition of a little aqueous potassium hydroxide. The precipitated solid was collected, washed with water and dried to give the title base (1.25 g), which was recrystallised three times from water/ethanol mixtures. The base was dissolved in hot ethanol (12 ml) and acidified with ethanolic hydrogen chloride to give the title compound as hydrochloride, one and a quarter hydrate (0.92 g) mp 278 °-81° C. (dec).

EXAMPLE 6

(Endo)-N-(8-methyl-8-azabicyclo[3.2.1]octan-3-yl)-1,8-ethano-1,4-dihydro-4-oxoquinoline-3-carboxamide A suspension of 1,8-ethano-1,4-dihydro-4-oxoquinoline -3-carboxylic acid (1.08 g, 5 mmol) and carbonyldiimidazole (0.89 g, 5.5 mmol) in dimethylformamide (15 ml) was stirred and heated at 80° C. for 1.25 hours to give a clear solution. (Endo)-3-aminotropane (0.7 g, 5 mmol) was then added in one portion and the reaction stirred at 80° C. for 2 hours. The reaction was ice-cooled and diluted with water (25 ml) and the precipitated product collected and recrystallised twice from ethanol:water (2:1) to give 0.7 g of the title base. The base was dissolved in hot ethanol (15 ml) and acidified with ethanolic hydrogen chloride to give the title compound as the hydrochloride (0.55 g), mp.>300° C.

EXAMPLE 7

(Endo)-N-(8-aza-8-methylbicyclo[3.2.1]octan-3-yl)1,4-dihydro-1,8-propanoquinolin-4-one-3-carboxamide The title compound was prepared following the procedure of Example 6 but replacing 1,8-ethano-1,4-dihydro-4-oxoquinoline-3-carboxylic acid by 1,8-propano-1,4-dihydro-4-oxoquinoline-3-carboxylic acid. The product was obtained as the hydrochloride, mp.>300° C.

EXAMPLE 8

(Endo)-N-(8-methyl-8-azabicyclo[3.2.1]octan-3-yl)-1,4-dihydro-4-oxo-1-n-propylquinoline-3-carboxamide 1,4-Dihydro-4-oxo-1-n-propylquinoline-3-carboxylic acid (1.58 g, 6.82 mmol) and triethylamine (0.7 g, 7 mmol) were dissolved in dichloromethane (20 ml), under an Argon blanket. Diphenylphosphinic chloride (1.6 g, 6.76 mmol) were added all at once with stirring. The solution was left for 6 h then (endo)-3-aminotropane (1.0 g, 7.14 mmol) and triethlamine (0.7 g, 7 mmol) were added. The solution was left for 3 days, then evaporated. The residue was dissolved in water and acidified with concentrated hydrochloric acid. The precipitate was filtered off, washed with water and discarded. The filtrate was basified with sodium carbonate and evaporated. The residue was triturated twice with ethyl acetate, the ethyl acetate evaporated, and the residue triturated with water (6 ml) and concentrated ammonia (1 ml) to give a white solid (1.34 g). This material (3.68 mmol) was dissolved in hot ethanol (15 ml) and oxalic acid dihydrate (0.47 g, 3.73 mmol) was added. The resulting solution was refrigerated overnight. The precipitate was collected, washed with ethanol and dried to give the title compound as the oxalate, half hydrate (1.24 g), m.p. 227°-231°.

EXAMPLES 9-14

Following the procedure of Example 1 but replacing 1,4-dihydro-1-methyl-4-oxoquinoline-3-carboxylic acid with the following reactants the following products were obtained:

| Example | | |
|---|---|---|
| 9. | Reactant: | 1,4-dihydro-1-ethyl-4-oxoquinoline-3-carboxylic acid. |
| | Product: | (endo)-N-(8-methyl-8-azabicyclo[3.2.1]octan-3-yl)-1,4-dihydro-1-ethyl-4-oxoquinoline-3-carboxamide, hydrochloride, hemihydrate, m.p 298-302° C. |
| 10. | Reactant: | 1,4-dihydro-1-(2-methoxyethyl)-4-oxoquinoline-3-carboxylic acid. |
| | Product: | (endo)-N-(8-methyl-8-azabicyclo[3.2.1]octan-3-yl)-1,4-dihydro-1-(2-methoxyethyl)-4-oxoquinoline-3-carboxamide, 1:1 fumarate m.p 243-245° C. |
| 11. | Reactant: | 9-Fluoro-6,7-dihydro-5-methyl-1-oxo-1H,5H-benzo[ij]quinolizine-2-carboxylic acid. |
| | Product: | (endo)-N-(8-methyl-8-azabicyclo[3.2.1]octan-3-yl)-9-fluoro-6,7-dihydro-5-methyl-1-oxo-1H,5H-benzo[ij]quinolizine-2-carboxamide, hydrochloride, quarter hydrate, m.p >320° C. |
| 12. | Reactant: | 1-cyclohexyl-1,4-dihydro-4-oxoquinoline-3-carboxylic acid |
| | Product: | (endo)-N-(8-methyl-8-azabicyclo[3.2.1]octan-3-yl)-1-cyclohexyl-1,4-dihydro-4-oxoquinoline-3-carboxamide, 1:1 oxalate, 1¼ hydrate, m.p 217° C. |
| 13. | Reactant: | 1-(cyclopropylmethyl)-1,4- |

|   Example |          |                                                                                                                                                                                                         |
|-----------|----------|---------------------------------------------------------------------------------------------------------------------------------------------------------------------------------------------------------|
|           | Product: | dihydro-4-oxoquinoline-3-carboxylic acid (endo)-N-(8-methyl-8-azabicyclo[3.2.1]octan-3-yl)-1-cyclopropylmethyl-1,4-dihydro-4-oxoquinoline-3-carboxamide, hydrochloride, 0.75 hydrate, m.p 164–166° C. (dec.) |
|       14. | Reactant:| 1-(4-fluorophenyl)-1,4-dihydro-4-oxaquinoline-3-carboxylic acid                                                                                                                                          |
|           | Product: | (endo)-N-(8-methyl-8-azabicyclo[3.2.1]octan-3-yl)-1-(4-fluorophenyl)-1,4-dihydro-4-oxoquinoline-3-carboxamide, hydrochloride, m.p. 240° (dec).                                                              |

EXAMPLE 15

Following the procedure of Example 1 but replacing (endo)-3-aminotropane with 1-azabicyclo[2.2.2]octan-3-amine (3-aminoquinuclidine) there is obtained N-(1-azabicyclo[2.2.2]octan-3-yl)-1,4-dihydro-1-methyl-4-oxoquinoline-3-carboxamide, hydrochloride, hydrate m.p. 179°–181° C.

EXAMPLE 16

(Endo)-N-(9-methyl-9-azabicyclo[3.3.1]nonan-3-yl)1,4-dihydro-1-ethyl-4-oxoquinoline-3-carboxamide A suspension of 1,4-dihydro-1-ethyl-4-oxoquinoline-3-carboxylic acid (1.52 g, 7 mmol) and triethylamine (0.7 g, 7 mmol) in dichloromethane (20 ml) was stirred at room temperature under argon for 1 h. Isobutyl chloroformate (0.96 g, 7.03 mmol) was added and the mixture stirred for 1 h. Triethylamine (1.4 g, 14 mmol) and (endo)-3-amino-9-methyl-9-azabicyclo[3.3.1]nonane dihydrochloride (1.58 g 6.96 mmol) were added. After 3 days the reaction was quenched with methanol and the solvents evaporated. The residue was triturated with water (10 ml) and concentrated ammonia (2 ml), the solid collected, washed with concentrated ammonia and dried. This material was converted to its 1:1 fumaric acid salt in IPA:methanol (2:1,15 ml) to give the title compound as the 1:1 fumarate, half hydrate (73.1%) m.p. 184°–185° C.

EXAMPLE 17

(Endo)-N-(9-Methyl-9-azabicyclo[3.3.1]nonan-3-yl-1-butyl-1,4-dihydro-4-oxo-quinoline-3-carboxamide 1,4-Dihydro-1-butyl-4-oxoquinoline-3-carboxylic acid was reacted with (endo)-3-amino-9-methyl-9azabicyclo[3.3.1]nonane by the procedure of Example 16 and the title compound obtained as the 1:1 maleate, m.p. 203°–205° C.

EXAMPLE 18

(Endo)-N-(8-Methyl-8-azabicyclo[3.2.1]octan-3-yl-1-ethyl-6-fluoro-1,4-dihydro-4-oxoquinoline-3-carboxamide 1,4-Dihydro-1-ethyl-6-fluoro-4-oxoquinoline-3-carboxylic acid is reacted with (endo)-3-aminotropane by the procedure of Example 16 and the title compound obtained as the hydrochloride, ¾ hydrate, m.p. 315°–317° C.

EXAMPLE 19

By following the procedures given above using appropriate reactants there are obtained:

(endo)-N-(8-methyl-8-azabicyclo[3.2.1]octan-3-yl)-1,4dihydro-1-cyclopropyl-4-oxoquinoline-3-carboxamide and the corresponding 1-cyclobutyl, 1-cyclopentyl, 1-tert.butyl and 1-(but-3-enyl) analogues;

(endo)-N-(8-methyl-8-azabicyclo[3.2.1]octan-3-yl)-1,4-dihydro-1-ethyl-6,7-methylenedioxy-4-oxoquinoline-3-carboxamide;

(endo)-N-(8-methyl-8-azabicyclo[3.2.1]octan-3-yl)-1,4-dihydro-1-ethyl-7-fluoro-4-oxoquinoline-3-carboxamide and analogues in which the 7-fluoro substituent is replaced by 7-trifluoromethyl; 8-fluoro; 6,7-difluoro and 6-chloro-8-methyl.

We claim:

1. A compound of the formula

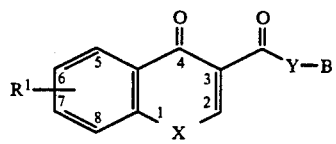

(I)

or a pharmaceutically acceptable acid addition salt thereof, in which $R^1$ represents hydrogen or one or more substituents selected from lower alkyl, hydroxy, lower alkoxy, halogen, methylenedioxy, halo(lower)alkyl, nitro, amino, (lower)alkylamino and di(lower)alkylamino;

X represents a group of formula —Z— which is connected to the 8-position of the aromatic ring so as to form a heterocyclic ring of 5–6 ring members wherein the ring members represented by Z are two or three methylene groups optionally substituted by one or more lower alkyl groups and the X position of the —Z— chain is N;

Y represents O or $NR^3$ where $R^3$ is hydrogen or lower alkyl and B represents a saturated azabicyclic ring, or an N-oxide thereof, wherein the saturated azabicyclic ring has the formula

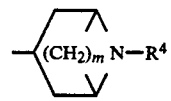

(II)

where m is 2 or 3 $R^4$ is hydrogen or (lower)alkyl.

2. A compound as claimed in claim 1 where m is 2 and $R^4$ is methyl.

3. A compound as claimed in claim 1 which is (endo)-N-(8-methyl-8-azabicyclo[3.2.1]octan-3-yl-1,8-ethano-1,4-dihydro-4-oxoquinoline-3-carboxamide or a pharmaceutically acceptable addition salt thereof.

4. A compound as claimed in claim 1 which is (endo)-N-(8-aza-8-methylbicyclo[3.2.1]octan-3-yl)-1,4-dihydro-1,8-propanoquinolin-4-one-3-carboxamide or a pharmaceutically acceptable addition salt thereof.

5. A pharmaceutical composition comprising an effective amount of a compound claimed in claim 1 in association with a pharmaceutically acceptable carrier.

* * * * *